United States Patent
Lindsay

(10) Patent No.: US 6,660,016 B2
(45) Date of Patent: Dec. 9, 2003

(54) INTEGRATED VEIN DISSECTOR AND CAUTERIZING APPARATUS FOR ENDOSCOPIC HARVESTING OF BLOOD VESSELS

(75) Inventor: Erin Jessica Lindsay, Manchester, MI (US)

(73) Assignees: Terumo Corporation, Tokyo (JP); Olympus Optical Company, Ltd., Hachioji (JP)

(*) Notice: Subject to any disclaimer, the term of this patent is extended or adjusted under 35 U.S.C. 154(b) by 0 days.

(21) Appl. No.: 10/100,079

(22) Filed: Mar. 19, 2002

(65) Prior Publication Data

US 2003/0181907 A1 Sep. 25, 2003

(51) Int. Cl.[7] .................................. A61D 1/02
(52) U.S. Cl. .................................... 606/159
(58) Field of Search ................... 606/110, 159, 606/169, 170, 206, 157, 158, 190

(56) References Cited

U.S. PATENT DOCUMENTS

| | | | |
|---|---|---|---|
| 5,569,291 A | * 10/1996 | Privitera et al. | 606/185 |
| 5,655,545 A | * 8/1997 | Johnson et al. | 128/898 |
| 5,695,514 A | 12/1997 | Chin | |
| 5,873,889 A | 2/1999 | Chin | |
| 5,908,420 A | * 6/1999 | Parins et al. | 606/51 |
| 5,913,866 A | * 6/1999 | Ginn et al. | 606/174 |
| 5,980,549 A | 11/1999 | Chin | |
| 6,004,335 A | * 12/1999 | Vaitekunas et al. | 606/169 |
| 6,019,771 A | 2/2000 | Bennett et al. | |
| 6,022,313 A | 2/2000 | Ginn et al. | |
| 6,030,406 A | 2/2000 | Davis et al. | |
| 6,179,854 B1 | 1/2001 | Nash et al. | |
| 6,193,653 B1 | 2/2001 | Evans et al. | |
| 6,203,559 B1 | 3/2001 | Davis et al. | |
| 6,206,823 B1 | 3/2001 | Kolata et al. | |
| 6,206,877 B1 | 3/2001 | Kese et al. | |
| 6,352,544 B1 | * 3/2002 | Spitz | 606/159 |
| 6,375,635 B1 | * 4/2002 | Moutafis et al. | 604/43 |

OTHER PUBLICATIONS

"Ultrasonic Dissection for Endoscopic Surgery," D. Gossot et al., *Surgical Endoscopy*, 1999, 13:412–417.
Booklet "SonoSurg: Ultrasosnic Surgical System," Olympus Optical Co., Ltd., Tokyo, Japan, Printed in Japan R276UB–0900.
"Endoscopic Vessel Harvesting," http://www.guidant.com/products/vesselharvesting.ht, Nov. 3, 2000, p. 1 of 1.
"Vasoview Uniport Plus," http://www.guidant.com/products/uniportplus.ht, Nov. 3, 2000, pp. 1–3.

* cited by examiner

*Primary Examiner*—Michael J. Milano
*Assistant Examiner*—Victor Nguyen
(74) *Attorney, Agent, or Firm*—Burns, Doane, Swecker & Mathis, LLP

(57) ABSTRACT

An endoscopic apparatus for harvesting blood vessels includes a endoscopic barrel including a plurality of lumens, one of the lumens being dimensioned for receiving an endoscope, a handle disposed at a proximal end of the endoscopic barrel, and at least one integrated member for dissecting and cauterizing a blood vessel. The at least one integrated member includes two fingers having distally curved ends. Movement of each of the fingers is independently controlled by a control mechanism disposed within the handle. More specifically, a control rod extends between the handle and each of the fingers such that movement of the control mechanism between a first position and a second position produces a predetermined movement of the respective finger.

15 Claims, 5 Drawing Sheets

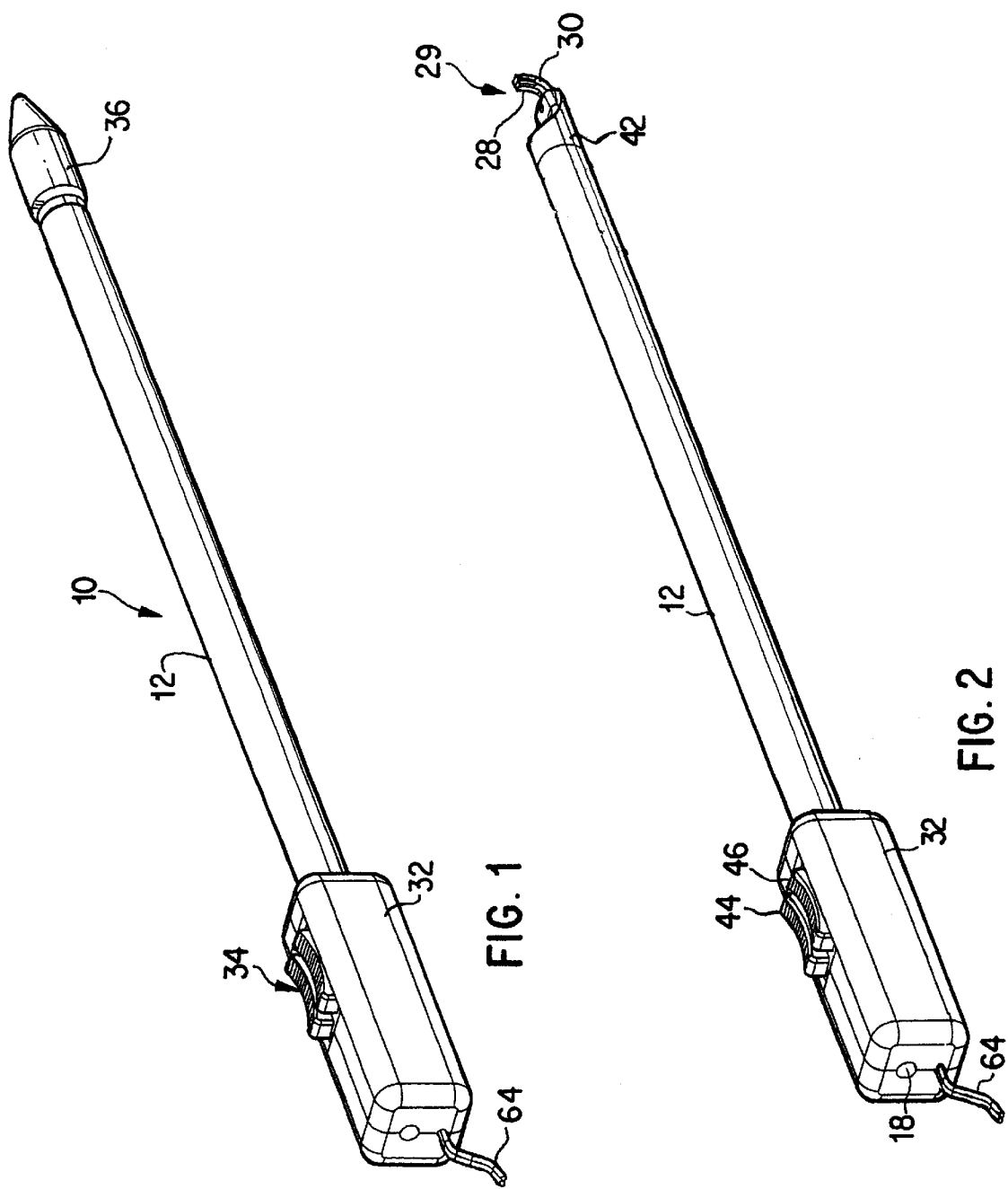

INTEGRATED VEIN DISSECTOR AND CAUTERIZING APPARATUS FOR ENDOSCOPIC HARVESTING OF BLOOD VESSELS

BACKGROUND OF THE INVENTION

The present invention relates to the harvesting of blood vessels and, more particularly, to methods and apparatus for endoscopic dissection and retraction of sections of blood vessels, such as saphenous veins, for use as a coronary artery bypass graft.

It is common during various surgical procedures, and most particularly during coronary artery bypass grafting (CABG), to remove or "harvest" a blood vessel or vessel section, such as an artery or vein, from its natural location in a patient's body and to use it elsewhere in the body. In CABG surgery, the blood vessel is used to form a bypass between an arterial blood source and the coronary artery that is to be bypassed. Often an artery proximate the heart, such as one of the internal mammary arteries, can be used as the bypass graft, although the saphenous veins in the legs, or a radial artery in an arm can also be used as well.

The conventional surgical procedure used to harvest a section of the saphenous vein, or the like, for use in the CABG surgery, is generally very traumatic to a patient. The procedure involves making a continuous incision in the leg for the full length of the desired vein section in order to provide adequate exposure for visualizing the vein and for introducing surgical instruments to sever, cauterize and ligate the tissue and side branches of the vein. The incision must then be closed by suturing or stapling along its length. Significant complications from this procedure may arise, such as infections, nerve damage, and hematomas. This type of surgical procedure is also known to produce undesirably scarring and can increase the patient's recovery time and hospital stay; thus adding to the overall cost of the CABG procedure.

In an attempt to overcome these problems, less-invasive techniques for harvesting blood vessels have been developed which employ only two small incisions, generally one at each end of the section of vessel to be removed. Primary dissection occurs by introduction of one or more surgical instruments through a first incision to create a working space and separate the vein from the surrounding tissue. Then further instruments are introduced into the generally limited working space to dissect the blood vessel from the connective tissue surrounding the section to be harvested. The side branches of the blood vessel are also clipped and/or cauterized. In order to remove the desired section of the blood vessel, a second small incision, or stab wound, is made at the distal end thereof and the distal end of the blood vessel section is ligated. The proximal end of the blood vessel section is then also ligated, thereby allowing the desired section to be completely removed through the first incision. An endoscopic instrument is generally required for such a procedure to enhance visualization of the vessel and the surrounding tissue and to properly position the surgical instrument. Example of such endoscopic instruments for harvesting blood vessels are shown in U.S. Pat. No. 6,193,653 to Evans et al. and U.S. Pat. No. 6,019,771 to Bennett et al.

Even though these less invasive techniques reduce the overall length of the incision, the trauma to the blood vessel section, the surrounding tissue and to the patient can still be severe. In particular, the repeated introduction of a plurality of surgical instruments through the incision into the enlarged space between the patient's skin and vein may also cause added irritation, damage and trauma to the vessel. Damage to the blood vessel or a side branch of the vessel is undesirable since the damage to the harvested section of the vessel must be repaired before it can be used as a graft and the potential for subsequent failure of the graft is increased.

Accordingly, it would be desirable to have a vessel harvesting procedure that can be carried out in a manner that reduces the trauma to the patient by minimizing the number of surgical instruments that must be inserted into the patient's body, by more rapidly and less traumatically detaching the blood vessel from surrounding tissue on all sides, and by providing a harvesting device and procedure that provides for more precise manipulation of the blood vessel by a surgeon.

SUMMARY OF THE INVENTION

The present invention provides an endoscopic apparatus for harvesting blood vessels which has an endoscopic barrel including a plurality of lumens, one of the lumens being dimensioned for receiving an endoscope. A handle is disposed at a proximal end of the endoscopic barrel and at least one integrated means for dissecting and cauterizing a blood vessel extends from a distal end of the endoscopic barrel.

In a preferred embodiment, the at least one integrated means comprises two fingers preferably having distal curved ends. More particularly, one of the fingers defines an inner finger and the other finger defines an outer finger such that, when the fingers are axially aligned, the inner and outer fingers form a shear plane therebetween for severing and cauterizing tissue, such as a blood vessel.

The movement of each finger is independently controlled by a control mechanism within the handle. The control mechanism includes, amongst other components, a control rod extending from the handle to each respective finger such that movement of the control mechanism between a first position and a second position produces a predetermined movement of the respective finger.

DETAILED DESCRIPTION OF THE FIGURES

These, and other objects, features, and advantages of the present invention will become more readily apparent to those skilled in the art upon reading the following detailed description, in conjunction with the appended drawings in which:

FIG. 1 is a perspective view of an integrated vein dissector and cauterizing apparatus for endoscopic harvesting of blood vessels according to a preferred embodiment of the present invention;

FIG. 2 is a perspective view thereof with the cone tip removed;

DETAILED DESCRIPTION OF THE PREFERRED EMBODIMENTS OF THE INVENTION

Figure 3:
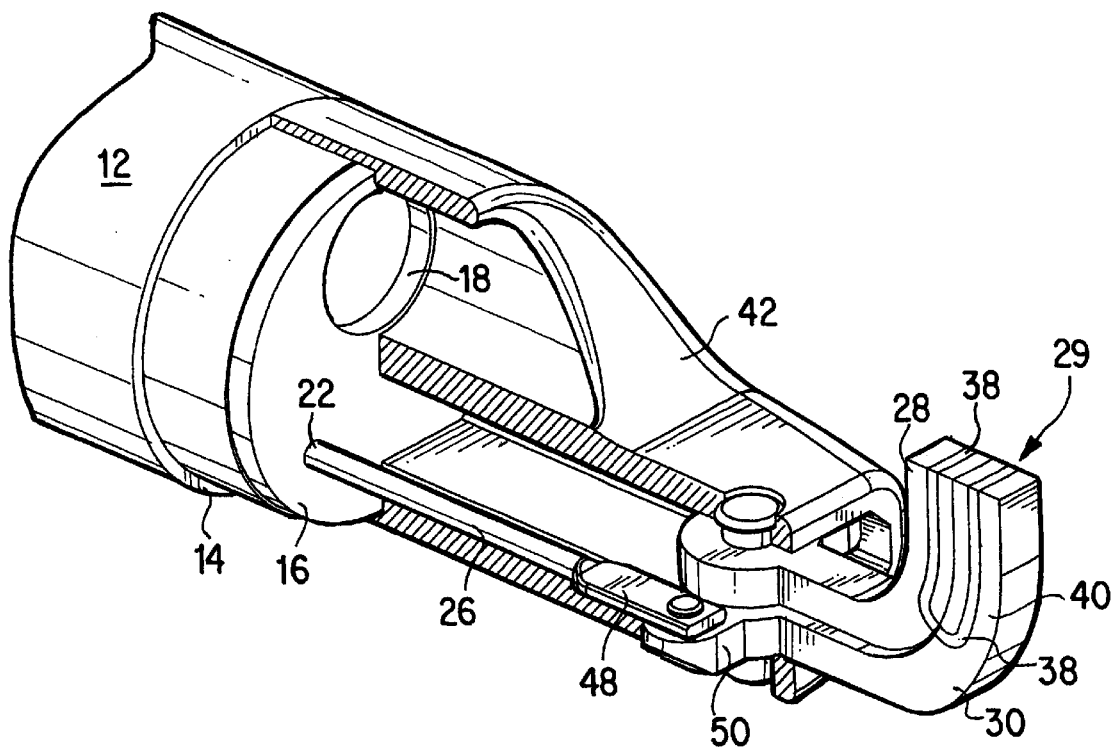
FIG. 3 is an enlarged perspective view of the vein dissector and cauterizing fingers of the apparatus shown in FIG. 2, when the fingers are axially aligned for severing a blood vessel.

An integrated vein dissector and cauterizing apparatus according to the present invention is shown generally by reference numeral 10 in FIG. 1. The integrated vein dissector and cauterizing apparatus 10 comprises an endoscopic tube 12, a handle 32 having a control mechanism 34, a removable cone 36, and at least one integrated means 29, preferably comprising inner and outer fingers 28, 30, for both dissecting and severing and cauterizing a desired blood vessel. The integrated apparatus 10 is utilized with the cone 36 in place when performing the primary dissection of the tissue from around a section of the desired blood vessel which is to be harvested, and thus creates a working space surrounding the selected section. The cone 36 is preferably formed from a transparent material, such as polycarbonate or other suitable material, so as to enable the surgeon to visualize the position of the integrated apparatus 10 through the lens of the endoscope.

Figure 4:
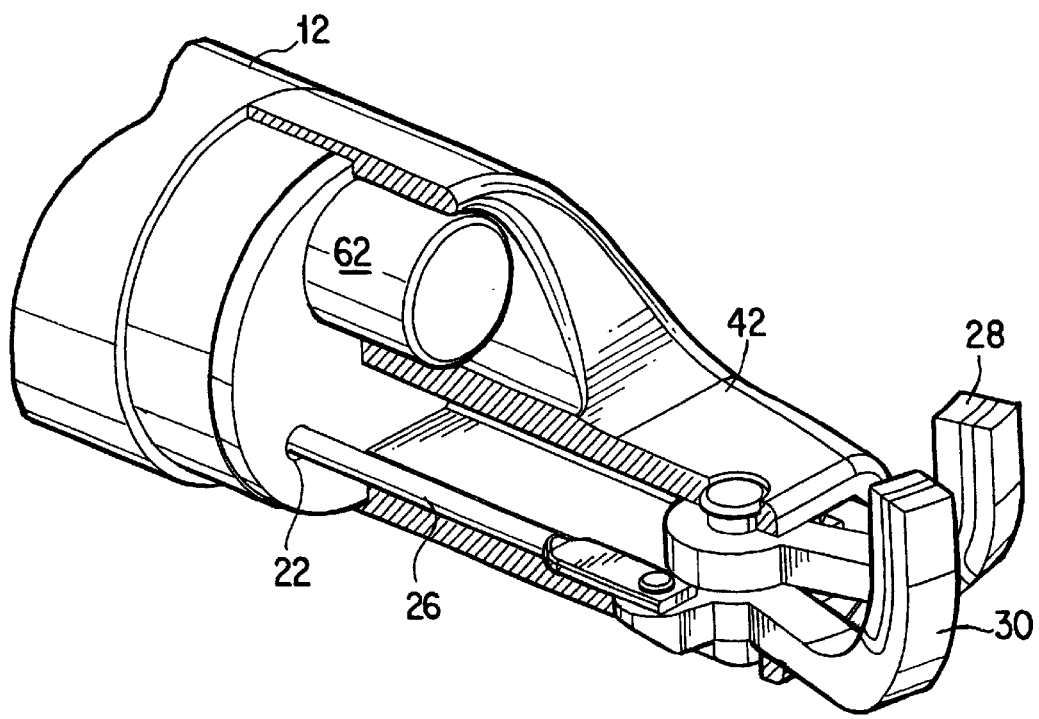
FIG. 4 is an enlarged perspective view of the fingers shown in FIG. 3, when the fingers are not axially aligned.

The endoscopic tube 12 preferably includes a flexible outer sheath 14, and a coaxial inner member 16 which forms at least two and more preferably three passages or lumens 18, 20, 22 extending the length thereof. Lumen 18 is generally the largest of the three lumens so as to accommodate the insertion of a conventional imaging system, or endoscope, having an optical lens arrangement 62 (FIG. 4) connected to an optical fiber and camera. Preferably, a zero degree endoscope is utilized, thereby allowing the surgeon to visualize the blood vessel directly in front of the apparatus 10, as discussed further below, but other endoscopes could of course also be used. The lumens 20 and 22 may accommodate control rods 24, 26, respectively, for movement of the inner and outer fingers 28, 30, as shown in FIGS. 3 and 4 and discussed further below. Alternatively, if only two lumens are provided within the endoscopic tube, the control rods may extend through a common lumen.

After performing the primary dissection and removing the integrated apparatus 10 through the first incision, the cone 36 may be removed from the distal end portion 42, thereby exposing the integrated means 29, and more preferably, the inner and outer fingers 28, 30, as shown in FIG. 2. Although the use of two fingers, as described below is a preferred embodiment of the present integrated means for dissecting and severing and cauterizing, one skilled in the art will recognize that other possible integrated means may utilize only one or more than two dissecting and cauterizing elements to form such an integrated means. Each of the fingers 28, 30 is preferably a bipolar electrode, although a monopolar electrode could of course also be used. More preferably, each finger includes a bipolar insulator 38 and an electrical conductor 40. As illustrated, each of the fingers 28, 30 may have a generally curved configuration generally resembling a hook portion on the terminal end thereof. The hook-shaped configuration, in combination with the separate and independent movement of each of the fingers 28, 30, enable the fingers to be used in removing connective tissue from the blood vessel.

Figure 5A:
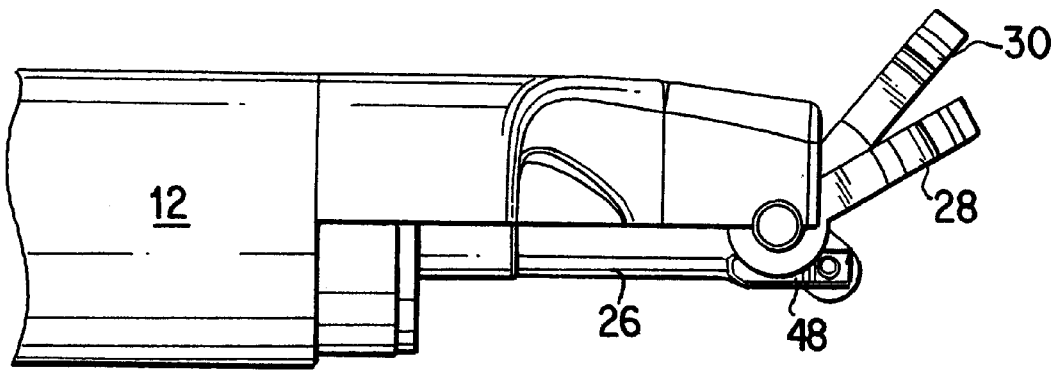
FIGS. 5A and 5B illustrate the fingers shown in FIG. 3 in the furthermost left and right positions, respectively.
Figure 5B:
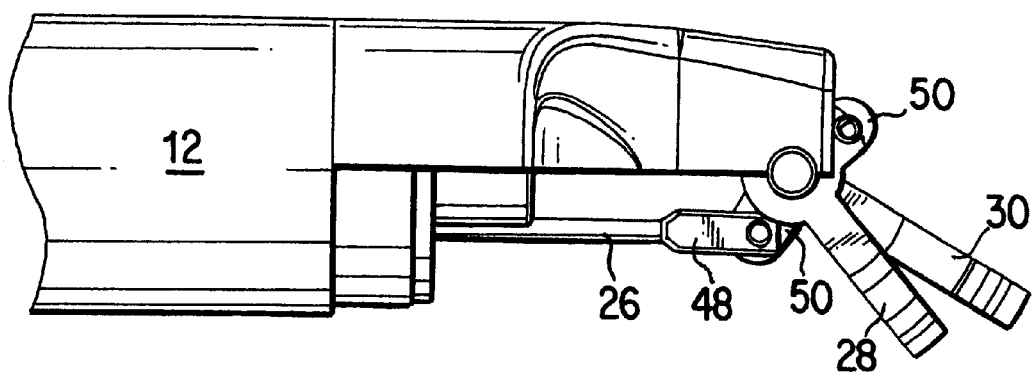
Figure 6A:
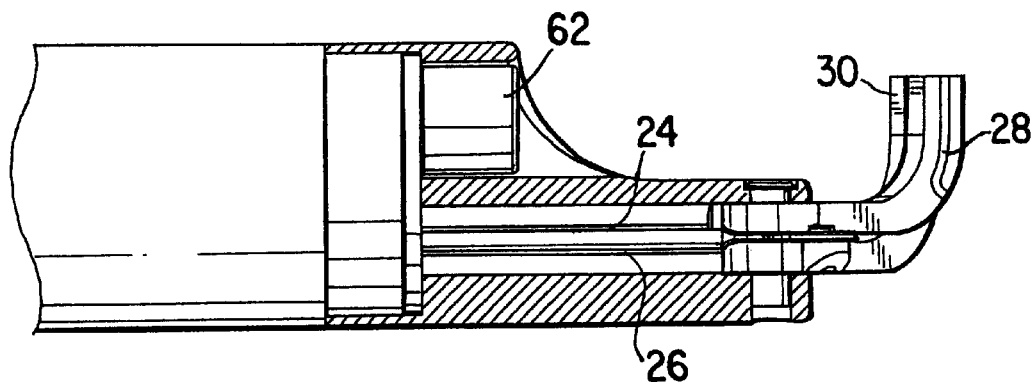
FIGS. 6A and 6B are cross sections of the fingers illustrated in FIGS. 5A and 5B.
Figure 6B:
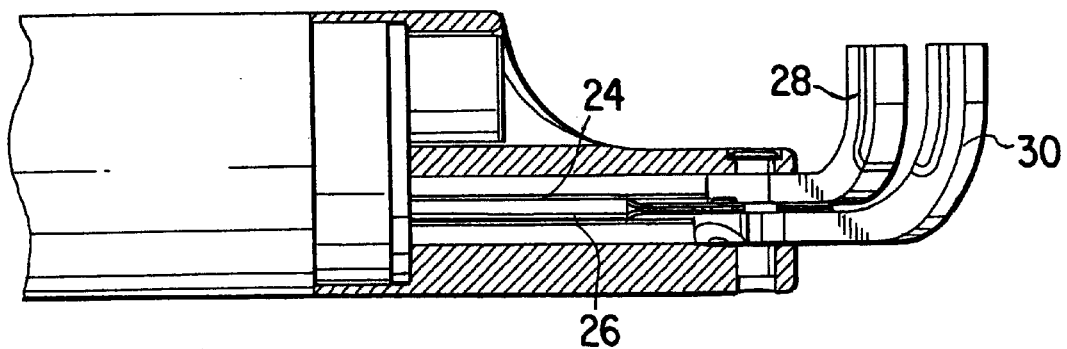

As shown best in FIGS. 5A and 5B, each of the fingers 28, 30 is capable of movement within an approximately 90° range. It should also be noted that one finger (the inner finger 28) is preferably shorter than the other finger (the outer finger 30) so as to define a shear plane therebetween when the fingers are axially aligned. This shear plane thus allows the fingers to perform a cutting or severing operation similar to that conventionally performed by surgical scissors or an anvil. In addition, however, because the fingers are also electrodes, the tissue between the fingers completes an electrical circuit and thus energizes the electrodes to thereby cauterize the tissue as it is being severed.

Figure 7:
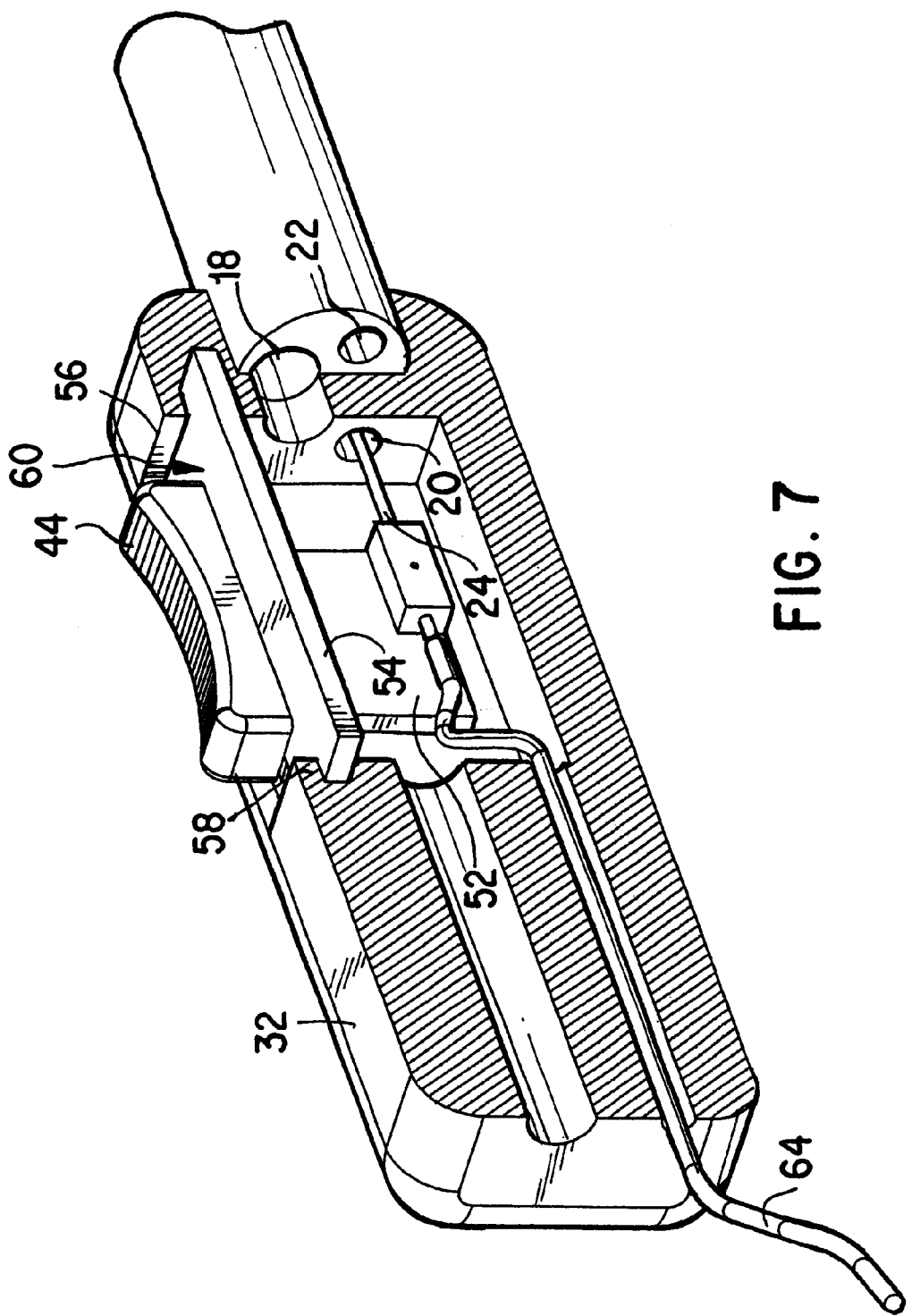
FIG. 7 is a cross section of the handle portion of the apparatus shown in FIGS. 1 and 2.

Referring also to FIG. 7, the movement of each of the fingers 28, 30 is preferably controlled by a control mechanism 34 disposed on the handle 32 of the apparatus 10. The control mechanism 34 preferably includes two separate finger control tabs 44, 46, control tab 44 controlling the movement of inner finger 28 within its 90° range of movement while control tab 46 controls outer finger 30 within its range of 90° movement. The control tabs 44, 46 are connected to the fingers 28, 30, respectively, by control rods 24, 26 which may extend through separate lumens 20, 22 within the endoscopic tube 12. The distal end of each control rod 24, 26 includes a link element 48 which connects the respective control rod to the attachment base 50 of the finger and thereby translates the motion of the control tab into the appropriate finger movement. As shown, the attachment bases 50 may extend from their respective fingers 28, 30 in opposing directions so as to reduce interference between the fingers.

Each of the finger control tabs 44, 46 may be moved in a sliding direction along a line parallel to the longitudinal axis of the endoscopic tube 12. Referring to FIG. 7, finger control tab 44 is shown in cross-section, it being understood that finger control tab 46 is similarly disposed. The handle 38 preferably includes a recessed area 60 on one surface thereof. The recessed area 60 thus defines a front stop 56 and a rear stop 58 which limits the movement of the control tab 44. The tab 44 may be mounted to a depending slider element 52 which extends downward through a top plate 54. Thus, the control tab 44 is preferably slidable along the top plate 54 within the recessed area 60, as defined between the front stop 56 and the rear stop 58.

The following description of the relative movement between a control tab and a respective finger is preferred for the illustrated embodiment; however, other arrangements would of course also be possible. Moving the control tab 44 to it's rearmost position within the recessed area 60 moves the inner finger 28 to a far left position and moving the control tab 46 to it's forwardmost position moves the outer finger 30 to a far left position, as viewed from above, in FIG. 5A. Similarly, moving the control tab 44 to it's forwardmost position while moving control tab 46 to it's rearmost position adjacent rear stop 58 moves the inner finger 28 and the outer finger 30 to a far right position, as viewed from above, in FIG. 5B. Each of the fingers 28, 30 can thus be positioned in a far left position or a far right position or anywhere inbetween. By manipulation of the control tabs 44, 46, a user can independently control the movement and position of each of the fingers 28, 30, thus allowing the fingers to be separated one from the other to form a U-shaped opening therebetween for tissue dissection, as shown in FIG. 4, or to be aligned one in front of the other, as shown in FIG. 3, when the fingers are to be used for severing and cauterizing. As mentioned above, disposed in each of the fingers 28, 30 is a cauterizing bipolar insulator 38. Each bipolar insulator 38 is electrically conducted and connected via a power cord 64 to a source of electric energy for cauterizing a severed end of a blood vessel, as will be explained below. The electrodes are preferably energized by a foot operable pedal, so as not to require use of the surgeon's hands.

The tabs 44, 46 can be placed in any position from front to back. Therefore, by independent positioning of the tabs, the fingers can separate and/or cross past each other as the operator sees fit. By biasing both fingers to the right, for example, the surgeon could create a separation useful in peeling connective tissue from a branch on the right side of the desired vein. By manipulating the tabs so as to cause the fingers to move towards each other, the fingers may act as a scissors and cauterize and cut that branch. To affect a scissor action, either the outer finger could go further to the right, eclipsing the inner finger, or the inner finger could go to the left, eclipsing the outer finger to affect a scissor action. The fingers can thus be placed in a right position, a left position, or a centerline position stationarily apart to form a "U" shaped branch or vein stripper, or by moving the tabs, the fingers may be caused to progress towards one another to close the gap, and, if a vein or vein branch is resident inbetween the fingers at this time, the sharp cutting edges on the adjacent shear plane will affect a severing action on the trapped tissue. If, at the same time the scissor edges are brought into contact with the tissue, the bi-polar electrodes are energized (such as by actuation of the associated foot pedal), the tissue will be burned, affecting a coagulation and lumen sealing of the vein or branch. The fingers 28, 30 of the present invention form a "U" shaped separated configuration having generally parallel side surfaces. It is thus believed that the parallel sides of the "U" shape are an improvement over a "V" shaped configuration which may tend to urge the blood vessel outward from a position disposed between the fingers, although a "V" shape could also be formed with the integrated apparatus 10 of the present invention.

In operation a section of a desired blood vessel, such as the saphenous vein, may be harvested using the integrated apparatus 10 of the present invention in the following manner. A small incision is formed at an appropriate location in a patient's leg adjacent the saphenous vein. With the cone 36 in position on the endoscopic tube, a distal end of the device 10 may be inserted through the incision and advanced forward to perform the primary dissection, so as to separate the tissue from the vein and create a working space therearound. As known in the art, gas insufflation, such as with carbon dioxide, may be used to maintain the working space in its expanded form.

After the primary dissection, the apparatus 10 is preferably withdrawn through the small incision and the removable cone 36 may be removed so as to expose the fingers 28, 30. After insertion through the incision once more, the inner fingers 28 and 30 may be separated, for example, with the inner finger disposed in the far left position while the outer finger 30 is disposed in the far right position so as to enable the vein to be disposed therebetween. Because the endoscope is preferably positioned above and to the rear of the fingers 28, 30, the optical lens 62 of the endoscope can clearly view the fingers 28, 30 and the tissue to be dissected; thereby providing optimal observation for guiding and operating the apparatus 10. In this manner the fingers 28, 30 can dissect the vein from the connective tissue and cut any side branches along the vein simply by movement of the fingers to the axially aligned position shown in FIG. 3. After removing the side branches and connective tissue, the integrated apparatus 10 may also be used for ligating the distal end of the section of the vein to be harvested. Initial positioning of the fingers 28, 30 in a centerline "U" configuration is also useful for such ligation and cutting of the distal end. Alternatively, a second small incision or stab wound may be made at the distal end. It is preferable, however, if a second incision is to be made, to do so when the removable cone is disposed on the endoscopic tube, such that the second stab wound may contact the cone 36 rather than risk damage to the desired blood vessel section. After ligation and cutting of the distal end of the desired blood vessel section, the integrated apparatus 10 may then also be used to ligate and cut the proximal end of the section, thereby allowing the desired section of the vein to be pulled through the first small incision.

The control tabs 44, 46 of the present invention allow the integrated apparatus 10 to be used with only one hand of the surgeon, thereby freeing a second hand, for example, to hold and reposition the patient's leg, which is frequently necessary in order to obtain the best angle for harvesting of the saphenous vein. Further, while slidable control tabs are shown as the preferred mechanism for obtaining the independent movement of the fingers, it should be apparent to one skilled in the art that other control mechanisms can of course also be used. Possible variations would include a thumb control for rotating pulleys to move cables and thereby operate the fingers independently. Further possible control mechanisms would include independent rack and pinion mechanisms which are again preferably controlled by the thumb of the user so as to enable single hand operation. Still further, both of the control rods 24, 26 and their respective lumens 20, 22, may be disposed within a separate inner member that is rotatable relative to the outer sheath 14 and the inner member 16; thereby allowing the entire finger assembly to rotate. In this instance, a rotation control mechanism would also be provided on the handle.

The present invention has now been described with reference to a preferred embodiment thereof. The foregoing detailed description has been given for clarity and understanding only. No unnecessary limitations are to be understood therefrom. It will be apparent to those skilled in the art that many changes can be made in the embodiment described without departing from the scope of the invention. Thus, the scope of the present invention should not be limited to the exact details and structures described herein, but rather by the structures described by the language of the claims, and the equivalents of those structures.

What is claimed is:

1. An endoscopic apparatus for harvesting a desired blood vessel comprising:
   an endoscopic barrel including at least two lumens, one of said lumens dimensioned for receiving an endoscope;
   a handle disposed at a proximal end of the endoscopic barrel;
   at least one integrated means for dissecting and cauterizing the desired blood vessel to be harvested; and
   a removable cone disposed over said at least one integrated means;
   wherein said removable cone is substantially transparent.

2. The apparatus of claim 1, wherein said at least one integrated means comprises two fingers.

3. The apparatus of claim 2, wherein said fingers include distal curved ends.

4. The apparatus of claim 2, wherein one of said fingers defines an inner finger and another of said fingers defines an outer finger such that, when said fingers are axially aligned, said inner and outer fingers form a shear plane therebetween for severing tissue.

5. The apparatus of claim 2, wherein movement of each said finger is independently controlled.

6. The apparatus of claim 5, wherein said handle includes a control mechanism for independently controlling each of said fingers.

7. The apparatus of claim 6, wherein said control mechanism comprises a movable control tab for each said finger disposed on said handle.

8. The apparatus of claim 7, wherein said control tabs are movable between a first position and a second position within a recessed area on said handle.

9. The apparatus of claim 8, wherein each said control tab further includes a slider disposed with said handle.

10. The apparatus of claim 9, wherein said slider is connected to a control rod, a distal end of the control rod being connected to one of said fingers such that movement of said control tab between the first position and the second position produces predetermined movement of said one of said fingers.

11. The apparatus of claim 10, wherein said endoscopic barrel includes three lumens, each of said control rods extending through a separate one of said lumens.

12. The apparatus of claim 1, wherein said at least one integrated means includes a bipolar electrode.

13. The apparatus of claim 1, wherein said at least one integrated means includes two extending members, each said member including a bipolar electrode such that upon severing tissue between said two extending members an electrical circuit is completed for cauterizing tissue therebetween.

14. The apparatus of claim 1, wherein said at least one integrated means includes a monopolar electrode.

15. The apparatus of claim 1, further comprising an endoscope extending through one of said lumens.

* * * * *